United States Patent [19]

Baillie

[11] 4,143,539
[45] Mar. 13, 1979

[54] APPARATUS AND METHOD FOR DETERMINING THE ATTRITION PROPERTIES OF A MASS OF SOLID PARTICLES

[75] Inventor: Lloyd A. Baillie, Homewood, Ill.

[73] Assignee: Atlantic Richfield Company, Philadelphia, Pa.

[21] Appl. No.: 887,409

[22] Filed: Mar. 16, 1978

Related U.S. Application Data

[63] Continuation-in-part of Ser. No. 660,207, Feb. 23, 1976, Pat. No. 4,081,249.

[51] Int. Cl.² .............................................. G01N 3/56
[52] U.S. Cl. ....................................... 73/7; 73/432 R; 55/270
[58] Field of Search .................... 73/7, 432 R; 55/270, 55/406

[56] References Cited

U.S. PATENT DOCUMENTS

| 1,899,774 | 2/1933 | Rothchild et al. | 73/7 |
| 3,636,772 | 1/1972 | Bennett | 73/7 X |
| 3,765,155 | 10/1973 | Courbon | 55/270 |

Primary Examiner—Herbert Goldstein
Attorney, Agent, or Firm—Frank J. Uxa

[57] ABSTRACT

An improved apparatus for determining the time rate of attrition of a mass of solid particles comprising a chamber; inlet and outlet providing for entrance and exit, respectively, to the chamber; a conduit providing communication between the inlet and outlet; an impeller located in the chamber to urge solid particles from the inlet in the general direction of the sidewall of the chamber; and a motor to provide rotation of the impeller.

Improved simulation of solid particle attrition in commercial cyclone separators is obtained.

13 Claims, 4 Drawing Figures

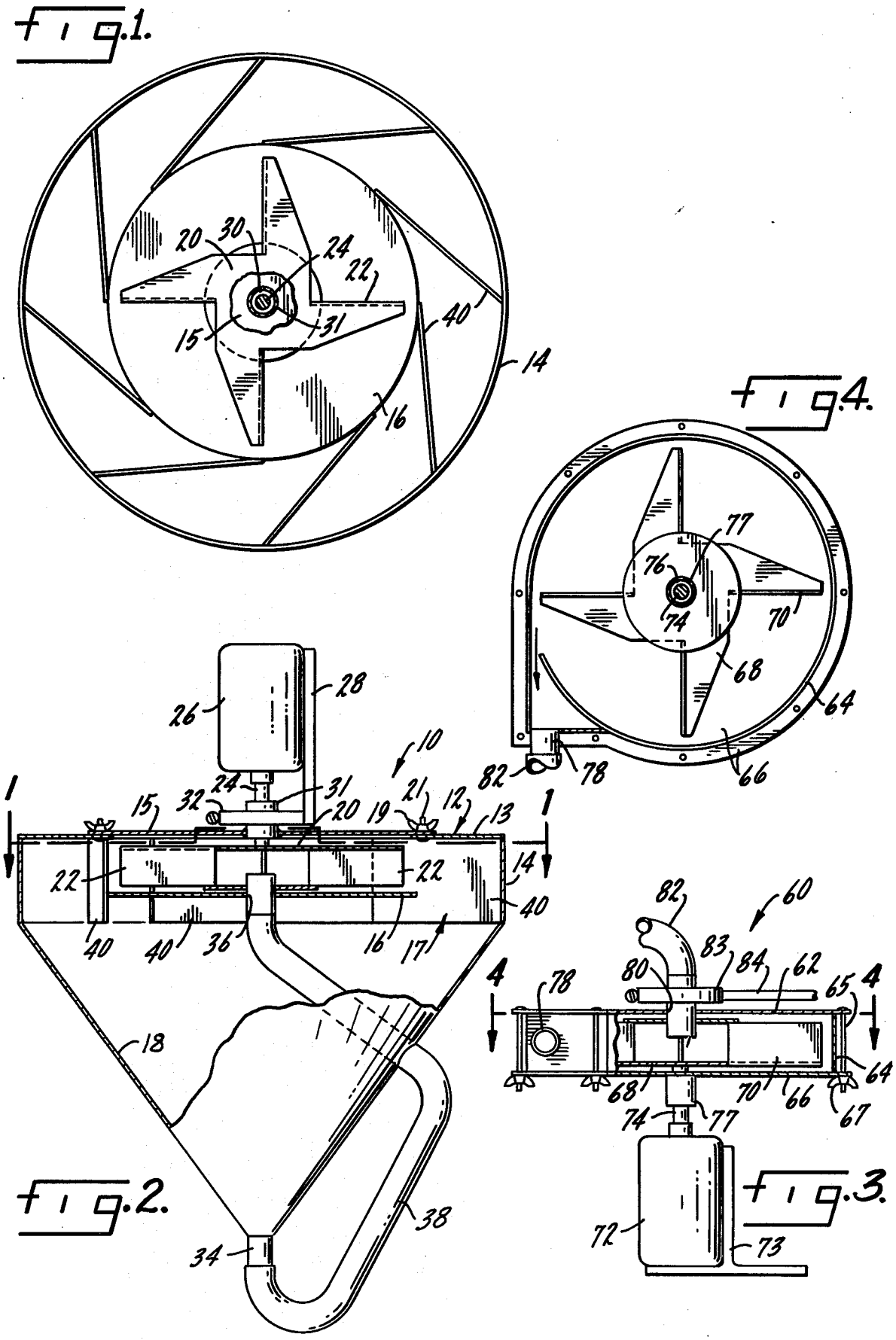

APPARATUS AND METHOD FOR DETERMINING THE ATTRITION PROPERTIES OF A MASS OF SOLID PARTICLES

This application is a continuation-in-part of application Ser. No. 660,207, filed Feb. 23, 1976, now U.S. Pat. No. 4,081,249 the specification of which is hereby incorporated by reference herein.

This invention relates to improved apparatus and methods for determining the tendency toward attrition and attrition resistance of solid particles, e.g., used to promote chemical conversions. More particularly, the invention relates to such improved apparatus and methods for determining the attrition properties of solid particles used to promote such conversions wherein mixtures of solid particles and vapor require separation.

In many instances throughout the process industries, chemical reactions occur which are promoted by relatively small, e.g., diameters in the range of about 10 microns to about 500 microns, catalyst particles, for example, in fluidized bed reactors. One process involving such catalyst particles is the catalytic cracking of higher boiling hydrocarbons to gasoline and other lower boiling components which is used extensively in the petroleum industry. Often, apparatus used for carrying out such chemical conversion, e.g., cracking, of a feedstock, e.g., hydrocarbon gas oil, involves a reaction zone where the relatively small catalyst particles and feedstock are contacted at chemical conversion, e.g., hydrocarbon cracking, conditions to form at least one chemical conversion product, e.g., hydrocarbons having a lower boiling point than the hydrocarbon feedstock. Often, while promoting the desired chemical conversion, the catalyst particles have deposited thereon material, e.g., carbon, coke and the like, which acts to reduce the catalytic activity of these particles. Apparatus which are used to restore the catalytic activity of such particles often include a regeneration zone where the deposit-containing solid particles are contacted with oxygen-containing vapor at conditions to combust at least a portion of the deposit material.

Operation of both of the systems referred to above involves the formation of a mixture of solid particles and vapor which requires separation. Therefore, both the apparatus for carrying out chemical conversion and the apparatus for restoring the catalytic activity of the solid catalyst particles include a separation zone wherein the mixture of solid particles and vapor formed in the reaction and regeneration zones, respectively, are at least partially separated. Such separation zones often involve conventional cyclone precipitators.

However, processing solid catalyst particles through such cyclone precipitators causes increased particle attrition. That is, the solid catalyst particles have an increased tendency to fall apart and/or form fines while being processed through a separation system, e.g., cyclone precipitator. The resulting particle "fines" are often of such a size that they cannot be reused to promote chemical conversion. Clearly, it is advantageous to provide for reduced attrition of solid catalyst particles.

In many instances, performing a full scale test using a conventional cyclone precipitator to determine the tendency toward attrition and attrition resistance of solid catalyst particles is impractical from, for example, time, space and economic considerations and the like. Therefore, it would be advantageous to have an apparatus to aid in predicting the attrition properties of a mass of solid particles.

Therefore, one object of the present invention is to provide apparatus and methods useful in predicting the attrition properties of a mass of solid particles. Other objects and advantages of the present invention will become apparent hereinafter.

An improved apparatus useful in determining the time rate of attrition of a mass of solid particles has now been discovered. This apparatus comprises (1) chamber means defined by substantially opposing first and second end walls and a, preferably, substantially circular, i.e., cylindrical, sidewall; (2) inlet means, preferably, substantially centrally located, in the chamber means to provide for entrance of the solid particles into the chamber means; (3) outlet means located in association with the chamber means to provide for withdrawing the solid particles from the chamber means; (4) conduit means providing communication between the inlet means and the outlet means to allow solid particles withdrawn from the chamber means in the outlet means to be reintroduced into the chamber means through the inlet means; (5) impeller means, preferably located substantially centrally, within the chamber means to urge the solid particles from the inlet means in the general direction of the sidewall of the chamber means; and (6) motor means in communication with the impeller means to provide for rotation of the impeller means.

This apparatus has been found to provide substantial benefits, e.g., improved simulation of solid particle attrition in commercially size cyclone separators or precipitators. Such improved simulation is obtained with a device which is relatively small, easy to operate and relatively maintenance free. In certain embodiments of the present invention, as will be described hereinafter, the present invention may be used to predict the time rate of attrition or attrition resistance of a mass of solid particles in a commercially sized cyclone separator or precipitator.

In one preferred embodiment of the present invention, the outlet of the present apparatus comprises a passageway located substantially tangentially to the sidewall of the chamber. In another preferred embodiment, the outlet comprises a hopper in fluid communication with the chamber through at least one hole in one end wall of the chamber, the hopper having an exit connected to the conduit. In this embodiment, the hole is preferably in the bottom end wall of the chamber and, more preferably, comprises an annular passageway between the chamber and the hopper.

In a still further preferred embodiment of the present invention, particularly useful when attempting to predict the attrition properties of a mass of solid particles in a commercially sized cyclone separator or precipitator, the present motor, preferably a variable speed motor, and impeller, are substantially independent of the chamber. That is, the motor and impeller rotate without substantially contacting any components, e.g., end walls and sidewalls, of the chamber.

Preferably, the chamber e.g., end walls and sidewall, is mounted or supported in such a manner as to be substantially free to rotate. One convenient way to provide the chamber with such substantially free rotatability is to support the chamber using support means, e.g., a ball bearing attached to a stationary support member, so that the chamber is substantially rotatable within the support means, e.g., around the axis of the ball bearing. This feature is particularly applicable in circumstances where it is desired to measure the force, e.g., torque, created by the circulation of solid particles and vapor through the present apparatus. Measurement of such forces will be discussed in detail hereinafter.

In an additional preferred embodiment, the inlet of the present apparatus is sized so that the velocity of the solid particles entering the chamber is substantially reduced relative to the tip velocity of the impeller, e.g., the impeller blades. More preferably, the entering velocity is less than about 50%, still more preferably, less than about 20% of the tip velocoty. This feature provides that a given solid particle is subjected to a minimum number of, e.g., no more than one, high velocity collisions, e.g., with the chamber sidewall, per cycle through the present apparatus. This closely simulates the movement of a given solid particle in a commercial cyclone separator or precipitator.

The present apparatus may be used to determine the attrition properties of any mass of solid particles. Such mass of solid particles preferably have a relatively small, e.g., in the range of about 10 microns to about 500 microns, weight average diameter. One particular application of the present invention involves determining the attrition properties of catalyst particles, such as those useful in catalytic hydrocarbon cracking, although other types of solid particles may be tested.

The catalyst particles useful in catalytic hydrocarbon cracking may be any conventional catalyst capable of promoting hydrocarbon cracking at the conditions present in the reaction zone, i.e., hydrocarbon cracking conditions. Conventionally, the catalytic activity of such particles is restored at the conditions present in the regeneration zone. Typical among these conventional catalysts are those which comprise alumina, silica, silica-alumina, at least one crystalline alumino silicate having pore diameters of from about 8Å to about 15Å and mixtures thereof. Because of the increased economic incentive for maintaining the particle size of zeolite-containing catalyst, it is preferred that the catalyst particles comprise from about 1% to about 50%, more preferably from about 5% to about 25%, by weight of at least one crystalline alumino-silicate having a pore diameter of from about 8Å to about 15Å. At least a portion of the alumina, silica, silica-alumina and crystalline alumino-silicate may be replaced by clays which are conventionally used in hydrocarbon cracking catalyst compositions. Typical examples of these clays include halloysite or dehydrated halloysite (kaolinite), montmorillonite, bentonite and mixtures thereof. These catalyst compositions may also contain minor amounts of other inorganic oxides such as magnesia, zirconia, etc. When the catalyst particles contain crystalline alumino-silicate, the compositions may also include minor amounts of conventional metal promoters such as the rare earth metals, in particular, cerium. Such catalyst compositions are commercially available in the form of relatively small particles, e.g., having diameters in the range from about 20 microns to about 200 microns, preferably from about 20 microns to about 150 microns.

In general, and except as otherwise provided for herein, the apparatus of the present invention may be fabricated from any suitable material or combination of materials of construction. The material or materials of construction used for each component of the present apparatus may be dependent upon the particular application involved. Of course, the apparatus should be made of materials which are substantially unaffected, except for normal wear and tear, by the conditions at which the apparatus are normally operated. In general, such material or materials should have no substantial detrimental effect on the feedstock being chemically converted, the chemical conversion product or products or the catalyst being employed.

These and other aspects and advantages of the present invention are set forth in the following detailed description and claims, particularly when considered in conjunction with the accompanying drawings in which like parts bear like reference numerals.

IN THE DRAWINGS

FIG. 1 is a top plan view of one embodiment of the present invention taken along line 1—1 of FIG. 2.

FIG. 2 is a side elevational view, partly in section, of one embodiment of the present apparatus.

FIG. 3 is a side elevational view, partly in section, of another embodiment of the present apparatus.

FIG. 4 is a top plan view of the embodiment shown in FIG. 3 taken along line 4—4 of FIG. 3.

Referring now to the embodiment of the present apparatus shown in FIGS. 1 and 2, the device, shown generally as 10, includes a substantially circular top end wall 12, a cylindrical sidewall 14 which has a substantially circular perimeter and a bottom end wall 16. The bottom end wall 16, which is substantially circular in configuration, does not extend fully to the sidewall 14, but rather, forms an annular passageway 17 with sidewall 14 to conical shaped hopper 18. Impeller 20, with blades 22 is located within the space defined by top end wall 12, sidewall 14 and bottom end wall 16. Impeller 20 is connected through shaft 24 to variable speed motor 26 which is firmly affixed to support element 28. Shaft 24 is designed not to contact top end wall 12. Thus, shaft 24 is surrounded by felt washer 30 which is enclosed in hollow tube 31 which, in turn, comes into contact with ball bearing 32 and acts to center shaft 24 so that no contact between shaft 24 and top end wall 12 is made. In addition, this mechanism provides that the impeller 20 is substantially independent of the top end wall 12 or any other element within the space defined by top end wall 12, sidewall 14 and bottom end wall 16. Further, hollow tube 31, which is attached, e.g., welded, to top end wall 12, is rotatable around the axis of ball bearing 32, thus permitting top end wall 12 and sidewall 14 to be similarly rotatable.

Conical hopper 18 terminates in outlet 34. Bottom end wall 16 is provided with a centrally located hole 36. One end of flexible tubing 38 is fitted into hole 36 while the other end of flexible tube 38 is attached to outlet 34. Flexible tubing 38 provides communication between hopper 18 and the space defined by top end wall 12, sidewall 14 and bottom end wall 16. Stationary baffles 40 are attached, e.g., welded, to the sidewall 14 at substantially the same acute angle from the tangent. The device 10 can also function without baffles 40. For example, a smooth cylindrical insert can be placed in the chamber, butting up against the edges of baffles 40.

Top end wall 12 is designed in two sections. Annular section 13 is permanently affixed to sidewall 14, while circular hatch section 15, attached to annular section 13 by a series of studs 21 and wing nuts 19, is removable to provide access to, for example, impeller 20.

The embodiment shown in FIGS. 1 and 2 functions as follows.

A mass of solid particles, e.g., fluid catalytic cracking particles, is placed in hopper 18. Variable speed motor 26 is activated thereby causing impeller 20 to rotate. As impeller 20 rotates, solid particles from outlet 34 pass through flexible tubing 38 into the space defined by top end wall 12, sidewall 14 and bottom end wall 16. The action of impeller 20 causes these solid particles to be propelled in a generally outwardly direction toward sidewall 14. Stationary baffles 40 act to reduce the velocity of these solid particles as the particles approach sidewall 14. As the particles approach sidewall 14, they fall into the annular passageway 17 defined by the bottom end wall 16 and sidewall 14 and proceed downward into the hopper 18 where they are recirculated back through outlet 34 and flexible hose 38 into the space defined by top end wall 12, sidewall 14 and bottom end wall 16. After a period of time, a given catalyst particle has proceeded around the apparatus as indicated several times. By determining particle size distribution both before and after the test period, the amount of particle break-up, e.g., attrition, that has occurred over this period of time can be determined. As will be explained hereinafter, correlations have been derived based upon, for example, the speed of the variable speed motor 26, which will aid in determining the attrition resistance of the solid particles.

Referring now to FIGS. 3 and 4, an additional embodiment of the present invention is shown generally as 60. The device 60 includes an internal substantially cylindrically shaped space defined by top end wall 62, sidewall 64 and bottom end wall 66. Located within the space so defined is impeller 68 having blades 70. Impeller 68 is centrally located within such space. Impeller 68 is powered by variable speed motor 72 acting through shaft 74. Variable speed motor 72 is firmly affixed to support element 73. Felt washer 76 surrounded by hollow tube 77 encompasses shaft 74 and acts to prevent shaft 74 from contacting bottom end wall 66. In this manner, variable speed motor 72, shaft 74 and impeller 68 are substantially independent of bottom end wall 66, sidewall 64 and top end wall 62. Sidewall 64 has a substantially tangential exit 78 whereas top end wall 62 is provided with hole 80. One end of flexible tubing 82 is fitted into hole 80 while the other end of flexible tubing 82 is attached to exit 78. Flexible tube 82 is supported in place by ball bearing 83 and support member 84. Ball bearing 83 is designed in conjunction with support member 84 to support top end wall 62, sidewall 64 and bottom end wall 66 and, in addition, allow these walls to be substantially rotatable around the axis of ball bearing 83.

In the embodiment shown in FIGS. 3 and 4, the bottom end wall 66 and top end wall 62 extend beyond sidewall 64. Studs 65 in top end wall 62 extend through holes in bottom end wall 66 and are attached thereto with wing nuts 67. In this manner, the device 60 can be disassembled, for example, for complete removal of the solid particles being tested.

Device 60 functions as follows. A mass of solid particles, e.g., fluid catalytic cracking particles, are placed in the space defined by top end wall 62, sidewall 64 and bottom end wall 66. Variable speed motor 72 is activated thereby causing impeller 68 to rotate. The action of impeller 68 causes the solid particles to be propelled in a generally outwardly direction toward sidewall 64. As the particles approach sidewall 64, at least a portion of such particles are caused to flow through exit 78 into flexible tubing 82 and thence into the space defined by top end wall 62, sidewall 64 and bottom end wall 66. The particles enter this space at a velocity which is reduced relative to the top speed of blades 70. After a period of time, a given catalyst particle has circulated through the device 60 several times and by determining the particle size distribution of the mass of solid particles before and after the test period, the amount of particle attrition resulting during the test can be determined. Correlations, as noted previously provide an additional measure of the attrition resistance of such solid particles.

The following examples clearly illustrate the present invention. However, these examples are not to be interpreted as specific limitations on the invention.

EXAMPLES 1 to 4

These examples illustrate certain of the advantages of the present invention.

A device 10 which propels a mixture of solid catalyst particles and air was used to simulate the movement of solid catalyst particles in various separators.

The device 10 involves top end wall 12, sidewall 14 and bottom end wall 16 defining a cylindrical chamber having an inside diameter of 17 inches. Sidewall 14 has a depth of 3 inches. Centrally mounted in the chamber is an impeller 20 having four blades 22. The impeller 20 has an overall diameter of 10 inches and a depth of 1.375 inches. The impeller 20 is driven by a variable speed motor 26 which is mounted above and outside the chamber as shown in FIG. 2. A series of eight baffles 40 surround the impeller. Each of these baffles 40 is 3 inches deep, 6 inches long and is welded to the interior of sidewall 14. Each of the baffles 40 extend from this surface a substantially uniform radial distance of 3 inches into the chamber. Also, each of the baffles 40 is situated at a substantially uniform acute angle relative to the tangent at the point of attachment to the chamber.

A conical hopper 18, situated directly below the chamber, is in fluid communication with the chamber by means of annular passageway 14 defined by sidewall 14 and the outer edge of bottom end wall 16. Bottom end wall 16 is situated directly below and is substantially co-extensive with the diameter of the impeller 20 plus blades 22 prevents catalyst particles from failling into the hopper 18 before the particles are forced out radially beyond the impeller 20 and blades 22. A piece of flexible one (1) inch O.D. tubing 38 provides fluid communication between the outlet 34 at the bottom of the hopper and the chamber. This tubing 38 enters the chamber from below through hole 38 in bottom end wall 16 and terminates in the space at the center of the impeller 20.

This device functions as follows. A quantity of catalyst particles, of known size distribution, is stored in the hopper 18. Air, from the surrounding environment is allowed to mix with the particles. The variable speed motor 26 is activated and causes the impeller 20 and blades 22 to rotate. Such rotation creates forces causing the catalyst particles-air mixture to flow through the tubing 38 into the chamber. The impeller 20 and blades 22 force the mixture in the chamber toward the peripheral interior surface of the sidewall 14. At least a portion of the solid particles strikes this surface. In any event, substantially all of the solid particles are returned to the hopper from the chamber and are recycled to the chamber through the tubing 38. After a period of time of operation, the solid catalyst particles in the hopper are analyzed for size to determine the degree of particle attrition which resulted from operation of the device 10.

In addition, a smooth cylindrical insert can be placed in the chamber. The perimeter of this insert is defined by the edges of the baffles 40 away from the interior peripheral surface of the sidewall 14. The insert has substantially the same depth as the baffles 40. Operation of the device 10 with this insert in place simulated the operation of a separator without arresting means, e.g., baffles, vanes and the like.

Velocities and mass circulation rates within the test device 10 are determined as follows:

The rotations per minute (rpm) of the variable speed motor 26 and shaft 24 is accurately measured by a strobe tachometer, which permits the calculation of the tangential component of velocity of the mixture of catalyst particles and air leaving the impeller 20 and blades 22. The impeller 20 is supported by the variable speed motor 26 and shaft 24, and contacted the chamber housing, e.g., top end wall 12, only through a felt washer 30 of negligible friction. The chamber housing is supported from a ball bearing 32, so that the torque caused by the circulation of air and catalyst particles can be measured. A string, having a weight M suspended therefrom, is attached to the chamber housing, e.g., sidewall 14, tangential to the outer perimeter of the impeller 20. Force is calculated from the lateral displacement of the suspended weight using the following equation:

$$\text{Force} = M \frac{X}{\sqrt{L^2 - X^2}}$$

wherein:
X = the lateral displacement of the weight from the chamber housing
L = the length of the string With the variable speed motor 26 in operation, the air circulation is blocked off by closing the tubing 38 with pinch clamps, and the force caused by friction and internal turbulence is measured. Then, the pinch clamps are removed, and the increase in force caused by circulating air is noted. Then, the catalyst is added and the incremental force caused by catalyst circulation is measured. Circulation rates of both air and catalyst are calculated from tangential force and tangential velocity as follows:

$$\text{Force (in grams)} = \frac{\text{Catalyst Circulation Rate (in grams per second)} \times \text{Total Catalyst Velocity (in centimeters per sec.)}}{980}$$

A catalyst particle undergoing radial acceleration by a rotating blade describes a logarithmic spiral, and will leave a rotating blade 22 of the impeller 20 at an angle of 45° to the tangent so that its radial and tangential velocities are equal, if it begins near the center and if there is no frictional drag against the blade 22. In this case, the co-efficient of friction of the catalyst particles is known from the angle of repose of a mass of such particles, so this can be used in the calculation of radial velocity. Tangential velocity of the catalyst particles is calculated as follows:

$V_t = 2\pi rw$; where r is the radius of the blade 22 and w is revolutions per unit time of the impeller 20. If the catalyst particles are introduced close to the center of the impeller, the radial velocity of the catalyst particles is:

$$V_r = (\sqrt{4 + a^2} - a)\pi rw;$$

where $a$ is the co-efficient of friction of the catalyst. The total velocity of the catalyst particles will be the vector sum of the tangential and radial velocities:

$$V = \sqrt{V_t^2 + V_r^2}$$

Using a value of 0.45 for $a$, the net velocity is 1.26 times the tangential velocity.

The catalyst particles used in this test device 10 were obtained from a commercial fluid bed catalytic hydrocarbon cracking reaction system. These particles had a composition which included about 15% by weight of alumino-silicate in a binder comprising silica-alumina. Before operation of the test device 10, these solid particles had the following size distribution.

| Size, Microns | % By Weight |
|---|---|
| 120+ | 12.0 |
| 100 – 120 | 18.0 |
| 80 – 100 | 24.0 |
| 60 – 80 | 23.0 |
| 40 – 60 | 5.6 |
| 20 – 40 | 15.9 |
| 0 – 20 | 1.5 |

Approximately 20 grams of these catalyst particles were placed in the hopper 18 of the test device 10 prior to each test.

A series of four (4) tests were run with the second of the motor set at 2300 rpm. In three of these tests, the baffles 40 remained uncovered, while in one test the smooth insert covered the baffles 40, as described above. Results of these tests were as follows:

| RUN | Configuration | Total Velocity, Ft./Sec. | Catalyst Circulation, gms./Sec. | Total Catalyst Circulated gms. | Incremental Fines-Production gms.* |
|---|---|---|---|---|---|
| 1 | Baffles Uncovered | 127 | 9.2 | 8280 | 0.23 |
| 2 | " | 127 | 12.8 | 11540 | 0.164 |
| 3 | " | 127 | 6.5 | 7790 | 0.15 |
| 4 | Smooth Insert In Place | 127 | 8.8 | 7940 | 0.88 |

*Incremental Fines Production is defined as the net increase in particles 20 microns or less in size which is apparent in the mass of catalyst after each test.

These results indicate clearly that the separation means including arresting means simulated by baffles 40 provides unexpected and substantial benefits. For example, when the test device 10 described above was configured to simulate such a separation means, i.e., runs 1, 2 and 3, incremental fines production was less than 20% the fines production with the device configured to simulate a smooth wall cyclone separator, i.e., run 4. Thus, the present apparatus and methods provide improved simulation of separation means whether or not including arresting means.

While this invention has been described with respect to various specific examples and embodiments, it is to be understood that the invention is not limited thereto and that it can be variously practiced within the scope of the following claims.

The embodiments of the invention in which an exclusive property or privilege is claimed are defined as follows:

1. An apparatus useful in determining the time rate of attrition of a mass of solid particles comprising:
   (1) chamber means defined by substantially opposing first and second end walls and a sidewall;
   (2) inlet means located in said chamber means to provide for entrance of said solid particles into said chamber means;
   (3) outlet means located in association with said chamber means to provide for withdrawing said solid particles from said chamber means;
   (4) conduit means providing communication between said inlet means and said outlet means to allow solid particles withdrawn from said chamber means in said outlet means to be reintroduced into said chamber means through said inlet means;
   (5) impeller means located within said chamber means to urge said solid particles from said inlet means in the general direction of said sidewall of said chamber means; and
   (6) motor means in communication with said impeller means to provide for rotation of said impeller means.

2. The apparatus of claim 1 wherein said sidewall is substantially circular, said inlet means and said impeller means are substantially centrally located within said chamber means.

3. The apparatus of claim 2 wherein said motor means is a variable speed motor.

4. The apparatus of claim 2 herein said outlet means comprises a passageway located substantially tangentially to said sidewall of said chamber means.

5. The apparatus of claim 4 wherein said motor means is substantially independent of said chamber means.

6. The apparatus of claim 5 wherein said inlet means is sized so that the velocity of said solid particles entering said chamber means is substantially reduced relative to the tip velocity of said impeller.

7. The apparatus of claim 6 wherein said chamber means is substantially free to rotate.

8. The apparatus of claim 2 wherein said motor is a variable speed motor.

9. The apparatus of claim 2 wherein said outlet means comprises a hopper means in communication with said chamber means through at least one hole in one end wall of said chamber means, said hopper having an exit means connected to said conduit means.

10. The apparatus of claim 9 wherein said motor means is substantially independent of said chamber means.

11. The apparatus of claim 10 wherein said inlet means is sized so that the velocity of said solid particles entering said chamber means is substantially reduced relative to the tip velocity of said impeller.

12. The apparatus of claim 11 wherein said chamber means is substantially free to rotate.

13. The apparatus of claim 12 wherein said motor is a variable speed motor.

* * * * *